(12) United States Patent
Martin et al.

(10) Patent No.: US 12,028,786 B2
(45) Date of Patent: Jul. 2, 2024

(54) POWER EFFICIENT ULTRA-WIDEBAND (UWB) TAG FOR INDOOR POSITIONING

(71) Applicant: Johnson Controls Tyco IP Holdings LLP, Milwaukee, WI (US)

(72) Inventors: Walter Andrew Martin, Ballymena (GB); Yucel Aydogan, Westford, MA (US); Irene Lam, Plainville, MA (US)

(73) Assignee: JOHNSON CONTROLS TYCO IP HOLDINGS LLP, Milwaukee, WI (US)

( * ) Notice: Subject to any disclaimer, the term of this patent is extended or adjusted under 35 U.S.C. 154(b) by 125 days.

(21) Appl. No.: 17/314,183

(22) Filed: May 7, 2021

(65) Prior Publication Data

US 2021/0266710 A1 Aug. 26, 2021

Related U.S. Application Data

(62) Division of application No. 16/735,322, filed on Jan. 6, 2020, now Pat. No. 11,026,067.

(Continued)

(51) Int. Cl.
*H04W 4/33* (2018.01)
*A41D 1/00* (2018.01)
(Continued)

(52) U.S. Cl.
CPC ............ *H04W 4/33* (2018.02); *A41D 1/005* (2013.01); *A61B 5/02055* (2013.01); *A61B 5/6804* (2013.01); *A63B 24/0062* (2013.01); *D03D 1/0088* (2013.01); *D03D 13/004* (2013.01); *G01S 1/024* (2013.01); *G01S 5/021* (2013.01); *G09B 19/0038* (2013.01); *H04W 4/029* (2018.02); *H04W 4/185* (2013.01); *H04W 4/80* (2018.02); *H04W 64/00* (2013.01); *A41B 1/08* (2013.01); *A41D 1/084* (2013.01);
(Continued)

(58) Field of Classification Search
CPC ......... H04W 4/33; H04W 4/029; H04W 4/80; H04W 4/185; H04W 64/00; G01S 1/024; G01S 5/021
USPC ...................................... 340/539.13
See application file for complete search history.

(56) References Cited

U.S. PATENT DOCUMENTS 10,484,833 B1 * 11/2019 Torborg ................. G01S 13/74
10,567,035 B1    2/2020 Torborg
(Continued)

OTHER PUBLICATIONS

Mohammadmoradi et al; "SRAC: Simultaneous Ranging and Communication in UWB Networks", 2019 15th International Conference on Distributed Computing in Sensor Systems (DCOSS), IEEE, May 29, 2019 (May 29, 2019), pp. 9-16, XP033599236, DOI: 10.1109/DCOSS. 2019.00025 (retrieved Aug. 16, 2019).

(Continued)

*Primary Examiner* — John A Tweel, Jr.
(74) *Attorney, Agent, or Firm* — ArentFox Schiff LLP

(57) ABSTRACT

A system provides ultra-wideband (UWB) positioning. The system exchanges ranging signals at a first rate between a UWB beacon and a UWB tag. The system then determines movement or location information of the UWB tag; and select, based on the movement or location information, a second rate for exchanging subsequent ranging signals between the UWB beacon and the UWB tag. The system then exchanges the subsequent ranging signals at the second rate between the UWB beacon and the UWB tag.

20 Claims, 5 Drawing Sheets

Related U.S. Application Data

(60) Provisional application No. 62/791,485, filed on Jan. 11, 2019.

(51) Int. Cl.

| | |
|---|---|
| *A61B 5/00* | (2006.01) |
| *A61B 5/0205* | (2006.01) |
| *A63B 24/00* | (2006.01) |
| *D03D 1/00* | (2006.01) |
| *D03D 13/00* | (2006.01) |
| *G01S 1/02* | (2010.01) |
| *G01S 5/02* | (2010.01) |
| *G09B 19/00* | (2006.01) |
| *H04W 4/029* | (2018.01) |
| *H04W 4/18* | (2009.01) |
| *H04W 4/80* | (2018.01) |
| *H04W 64/00* | (2009.01) |
| *A41B 1/08* | (2006.01) |
| *A41D 1/084* | (2018.01) |
| *A41D 1/089* | (2018.01) |
| *A61B 5/024* | (2006.01) |
| *A61B 5/08* | (2006.01) |
| *A61B 5/11* | (2006.01) |
| *A61B 5/145* | (2006.01) |
| *A61B 5/389* | (2021.01) |
| *A63F 13/212* | (2014.01) |
| *A63F 13/285* | (2014.01) |

(52) U.S. Cl.
CPC .......... *A41D 1/089* (2018.01); *A61B 5/02438* (2013.01); *A61B 5/08* (2013.01); *A61B 5/11* (2013.01); *A61B 5/14517* (2013.01); *A61B 5/389* (2021.01); *A63B 2024/0096* (2013.01); *A63F 13/212* (2014.09); *A63F 13/285* (2014.09); *A63F 2300/1012* (2013.01); *A63F 2300/1037* (2013.01); *A63F 2300/8082* (2013.01)

(56) References Cited

U.S. PATENT DOCUMENTS

| | | | |
|---|---|---|---|
| 11,026,067 B2 * | 6/2021 | Martin | .................... G01S 5/02 |
| 2012/0220233 A1 | 8/2012 | Teague et al. | |
| 2016/0158625 A1 * | 6/2016 | DeAngelis | ............ H04W 4/023 340/539.13 |
| 2017/0131383 A1 * | 5/2017 | Bartov | .................. G01S 13/765 |
| 2019/0228632 A1 | 7/2019 | Hassey | |

OTHER PUBLICATIONS

Extended European Search Report for EP20151300 mailed May 28, 2020.

\* cited by examiner

POWER EFFICIENT ULTRA-WIDEBAND (UWB) TAG FOR INDOOR POSITIONING

CROSS-REFERENCE TO RELATED APPLICATION(S)

This application is a divisional of U.S. Non-Provisional application Ser. No. 16/735,322, entitled "POWER EFFICIENT ULTRA-WIDEBAND (UWB) TAG FOR INDOOR POSITIONING" and filed Jan. 6, 2020, which claims the benefit of U.S. Provisional Application Ser. No. 62/791,485, entitled "POWER EFFICIENT ULTRA-WIDEBAND (UWB) TAG FOR INDOOR POSITIONING" and filed Jan. 11, 2019, all of which are expressly incorporated by reference herein in their entirety.

BACKGROUND

The present disclosure relates generally to systems and methods including or utilizing indoor positioning, and more particularly, to systems and methods including power efficient tags for indoor positioning.

Generally, ultra-wideband (UWB) technology may be used for determining a position of an object in a space based on time of flight (TOF) of radio-frequency (RF) signals between a reference and a target. Due to its operating frequencies, which allows for reliable signal transmission and reception in an environment having obstacles in the signal path, UWB technology may provide accurate positioning. For example, UWB technology may enable positioning with an accuracy of few centimeters or even few millimeters.

Based on this high level of accuracy and ability to track objects indoors, UWB technology may be used in control systems that track the position of objects that may move into and/or within indoor spaces. Such systems may include, but are not limited to, building control systems and/or building security systems.

Current solutions, while addressing the increased demand for accuracy in indoor positioning, suffer the drawback of not being practical to use for highly mobile objects due to the power required to maintain the UWB signaling. In one use case, for example, building control and/or security systems may be interested in tracking the position of a person within a building, which requires the person to carry a tag or fob having UWB technology. Such a tag or fob requires a battery to provide power for the UWB signaling. Current solutions provide a less-than-desirable user experience, however, as the tag or fob may be relatively large and heavy, and thus inconvenient for the person to carry. Alternatively, the size of the battery may be reduced, but the user experience is again not desirable as the tag or fob requires frequent recharging or replacing of the battery.

Thus, improvements are desired in control systems using UWB positioning.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

The present disclosure provides systems, apparatuses, and methods for ultra-wideband (UWB) positioning.

In an aspect, a method of UWB positioning includes exchanging ranging signals at a first rate between a UWB beacon and a UWB tag; determining movement or location information of the UWB tag; selecting, based on the movement or location information, a second rate for exchanging subsequent ranging signals between the UWB beacon and the UWB tag; and exchanging the subsequent ranging signals at the second rate between the UWB beacon and the UWB tag.

In another aspect, a UWB beacon apparatus includes a UWB communication component configured for exchanging ranging signals at a first rate with a UWB tag; and a controller. The controller is configured for determining movement or location information of the UWB tag; and selecting, based on the movement-related information or the location-related information, a second rate for exchanging subsequent ranging signals between the UWB beacon and the UWB tag. The UWB communication component is further configured for exchanging the subsequent ranging signals at the second rate between the UWB beacon and the UWB tag.

In a further aspect, a UWB beacon apparatus includes a processor and a memory coupled to the processor and storing instructions. The instructions, when executed by the processor, cause the processor to exchange ranging signals at a first rate between a UWB beacon and a UWB tag; determine movement or location information of the UWB tag; select, based on the movement or location information, a second rate for exchanging subsequent ranging signals between the UWB beacon and the UWB tag; and exchange the subsequent ranging signals at the second rate between the UWB beacon and the UWB tag.

In yet another aspect, a UWB tag apparatus includes a communication component configured for: exchanging ranging signals at a first rate with a UWB beacon, causing the UWB beacon to determine movement or location information of the UWB tag, and select, based on the movement-related information or the location-related information, a second rate for exchanging subsequent ranging signals between the UWB beacon and the UWB tag; and exchanging the subsequent ranging signals at the second rate with the UWB beacon.

In a further aspect, a UWB tag apparatus includes a processor and a memory coupled to the processor and storing instructions. The instructions, when executed by the processor, cause the processor to exchange ranging signals at a first rate with a UWB beacon, causing the UWB beacon to determine movement or location information of the UWB tag, and select, based on the movement-related information or the location-related information, a second rate for exchanging subsequent ranging signals between the UWB beacon and the UWB tag; and exchange the subsequent ranging signals at the second rate with the UWB beacon.

In another aspect, a positioning method includes exchanging, by a beacon, UWB ranging signals with a tag having a UWB communication component; determining a relative location of the tag based on the UWB ranging signals received by the beacon from the tag; calibrating a non-UWB positioning system based on the relative location; and tracking the tag by the non-UWB positioning system.

In a further aspect, a positioning method includes detecting a position of a UWB tag by a non-UWB positioning system; determining a relative location of the UWB tag with reference to a point of interest based on the detected position; exchanging ranging signals with the UWB tag, by a UWB beacon, in response to the relative location being within a proximity threshold of the point of interest; and tracking the relative location of the UWB tag with reference to the point of interest based on the ranging signals received by the UWB beacon from the UWB tag.

In another aspect, an authentication method includes determining a location of a UWB tag based on signals received by a UWB beacon from the UWB tag; determining an identifier (ID) associated with the UWB tag; determining biometric data of an entity substantially located at the location of the UWB tag; and authenticating the entity in response to the biometric data being associated with the ID associated with the UWB tag.

In a further aspect, a security method includes determining a security event in a monitored area; transmitting ranging signals, by one or more UWB beacons, to query a location of UWB tags in the monitored area; and determining whether a UWB tag located in the monitored area by the UWB beacons is associated with the security event.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

The disclosed aspects will hereinafter be described in conjunction with the appended drawings, provided to illustrate and not to limit the disclosed aspects, wherein like designations denote like elements, and in which.

DETAILED DESCRIPTION

Figure 1:
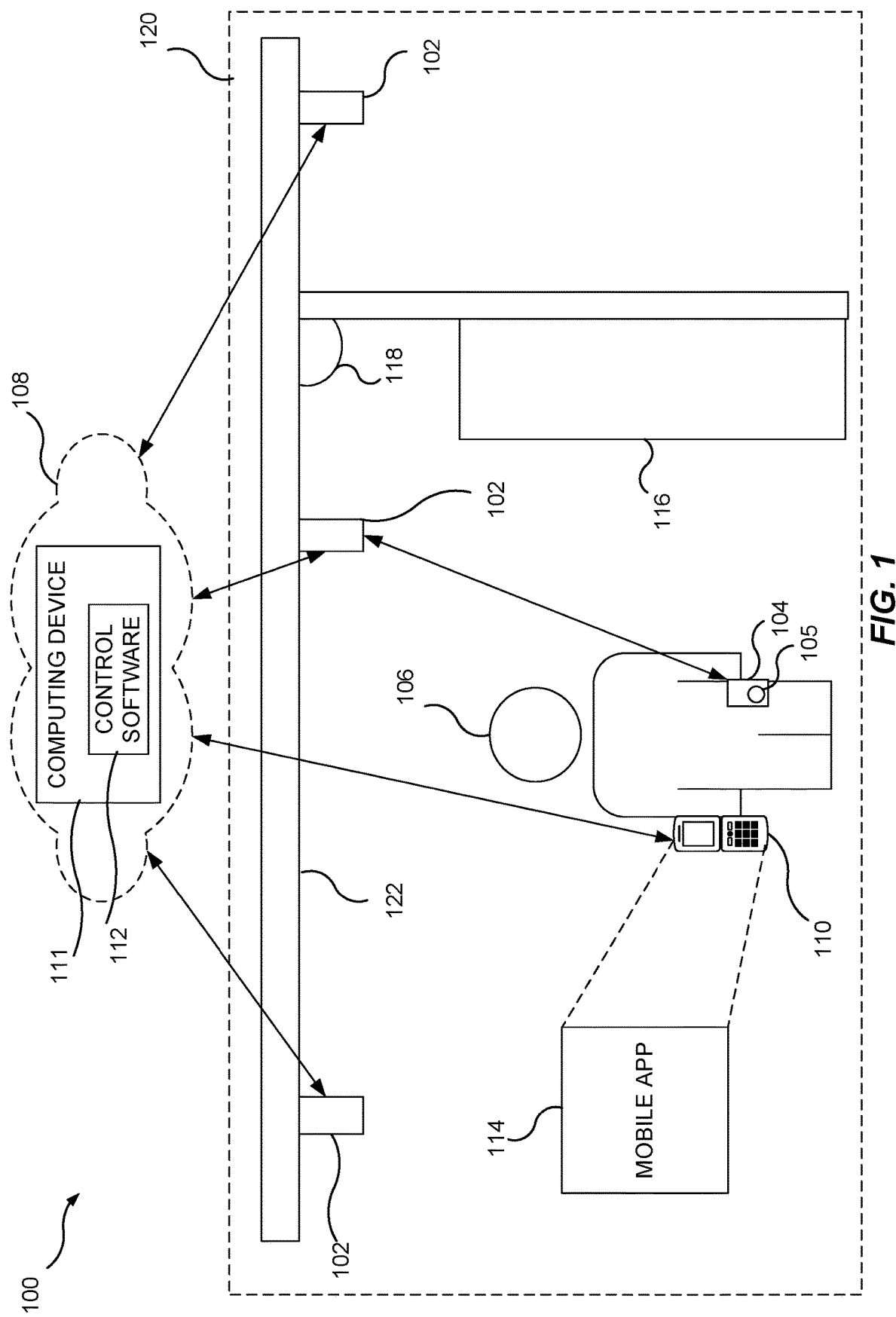
FIG. 1 is a schematic diagram of an example ultra-wideband (UWB) positioning system.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known components may be shown in block diagram form in order to avoid obscuring such concepts.

Aspects of the present disclosure provide an ultra-wideband (UWB) indoor positioning system including UWB tags configured to communicate in one or more power efficient manners. The present solutions may thereby reduce UWB tag size and/or increase UWB tag life. For example, the UWB tags may communicate UWB signals, in one or more of the UWB frequency bands, with UWB beacons installed across an indoor space. In some cases, such as based on Federal Communication Commission (FCC) standards, a UWB signal may be a signal that occupies a portion of a frequency spectrum that is greater than 20% of the center carrier frequency, or that has a bandwidth greater than 500 MHz. Moreover, a UWB signal may be transmitted in pulses over the entire UWB bandwidth, and as such UWB signaling may have a pulse rate. For instance, in some cases, a UWB signal may include a signal with ultra-short pulses, e.g., <1 ns, with a low duty cycle, e.g., <0.5%, capable of being simultaneously transmitted over a wide range of frequencies, e.g., 3.1 to 10.6 GHz, and having a large bandwidth, e.g., >500 MHZ.

In some aspects, the battery life of the UWB tags may be extended by controlling their transmission rate and/or by controlling the rate of UWB ranging signals transmitted by the UWB beacons to query the location of the UWB tags. For example, the rate of UWB ranging signaling may vary based on a location of a UWB tag, based on a distance of a UWB tag to a point of interest, based on movement or a direction of movement of a UWB tag, or some combination of these factors. In some implementations, for instance, a UWB tag located relatively far from a point of interest in the building (which may include the UWB beacon), or in a building location deemed lower priority for accurate positioning, may have a relatively low rate of ranging signaling as compared to a UWB tag located closer to the point of interest or in another building location having a higher priority for accurate positioning. Further, in some implementations, the present systems and method may increase the rate of ranging signaling in response to movement of the UWB tag and/or in response to the movement being toward the point of interest in the building. In some cases, the building location and/or point of interest may be defined by a virtual geographic boundary, such as based on geo-fencing information.

Some aspects may further use the accurate and power efficient UWB positioning provided by the present disclosure to periodically calibrate and/or improve the accuracy of other positioning systems tracking the UWB tags. For instance, examples of such other, less accurate positioning systems that may be used to track a tag include a magnetometer and/or other wireless positioning system that utilizes received signal strength measurements to determine the position of the tag. In some implementations, for example, the UWB positioning systems and methods described in this disclosure may be used in combination with other devices, such as a personal wireless communication device of a person associated with a UWB tag, to increase location determination accuracy of a less accurate positioning system such as a phone-based positioning system (e.g., terrestrial systems, such as WiFi, Bluetooth, Bluetooth Low Energy (BLE), and/or satellite based systems, such as a Global Positioning System (GPS) or Global Navigation Satellite System (GLONASS)).

Unlike other positioning systems that rely on received signal strength measurements for location determination, which can be inaccurate in indoor environments that include a lot of structures that can disperse or reflect the signal, the present UWB indoor positioning system takes advantage of the wideband nature of the UWB signalling to accurately determine location. Such received signal strength based positioning systems may include, but are not limited to, WiFi, Bluetooth, and BLE positioning systems. In the present UWB indoor positioning system, UWB beacons are configured for communication with UWB tags to measure a time of arrival (TOA) and/or a time difference of arrival (TDOA) of the wideband signaling, which enables the system to triangulate very accurate location of the tags within an indoor space. For example, the position of the tag may be determined with an accuracy of few centimeters or even millimeters. The wideband and pulsing characteristics of the UWB ranging signaling of this disclosure enable the transmitted signals to be received, even in an indoor environment with obstructions in the line of sight between the UWB tag and the UWB beacon.

In further aspects relating to controlling the rate of ranging signaling, the UWB tag of this disclosure may be used in combination with a mobile computing device, such as a smart phone or tablet, configured to execute a mobile application associated with the UWB tag. For example, such a mobile application may enable or assist in building environment and/or security control functions. In this case, the rate of ranging signaling, and hence a frequency of refreshing a location of the UWB tag, may vary depending on if the mobile application is executing or not. For instance, the rate of ranging signaling may be lower when the mobile application is not executing as compared to when the mobile application is executing.

In additional aspects, the accurate and power efficient location determination provided by the present disclosure may be used, for example, by a control system to control one or more building systems and/or security systems. For example, the position of a tracked object, such as a person, moving indoors may be used to efficiently condition the environment in a building based on the location of occupants, e.g., to adjust lighting, air conditioning, and/or to perform presence/security monitoring (e.g., responsive to an alarm or detection of an object in the building, the UWB beacon performing ranging signalling to identify and locate UWB tags in the area of the alarm/detection), and/or to provide privileges to the occupants of a building based on an identified UWB tag being correlated to another authentication factor (e.g., identification by a camera or sensor or other security equipment), e.g., to open an entrance door, unlock a resource such as a computer, printer, or other machine, etc.

More specific example cases of using the power efficient UWB indoor positioning techniques provided by the present disclosure include, but are not limited to, one or any combination of:

Determining proximity (using heading and velocity data) to a point of interest and increasing UWB transmission rate to achieve position accuracy such as for access control;

Using UWB to periodically transmit to re-calibrate inaccurate phone-based location technologies, such as magnetometer, WiFi, BLE;

Providing a combined technology, e.g., BLE and UWB, tag, where the UWB technology transmits periodically to correct BLE drift in position determination, including a case where the beacons have combined BLE/UWB technology;

Combining UWB beacons with fixed security equipment, such as CCTV cameras;

Activating tags by a local beacon to enable use cases such as crossing a tripwire, objects detected by camera, etc., where in response to an alarm input the beacon requests UWB tags in the area to transmit their location to help to ensure what has been detected is allowed;

Using the UWB tag positioning information as part of a 2 factor authentication, such as but not limited to a case where a camera detects a face, and in response a UWB beacon requests UWB tags in the area to transmit to determine their location such that a tag can be correlated to the detected and recognized face;

Using an accelerometer in a UWB tag to control location transmission rates, e.g., where transmission rates can be increased when the UWB tag is moving;

Using geo-fencing to control the rate of UWB ranging signaling between UWB beacons and UWB tags, e.g., such as a case where only the UWB beacons within a specified range of the UWB tags send signals; and/or Controlling a frequency of a location refresh based on feedback from a mobile application associated with a UWB tag, e.g., if a user is not logged in to the mobile application and/or if the mobile application is not executing and/or if the mobile application is running in the background, then less frequent location updates are performed as compared to if the user is logged in to the mobile application and/or if the mobile application is executing and/or if the mobile application is running in the foreground, respectively.

It should be understood that the above list of use cases are only some of a plurality of possible use cases of the present techniques.

Turning now to the figures, example aspects are depicted with reference to one or more components described herein, where components in dashed lines may be optional.

Referring to FIG. 1, in one non-limiting aspect, a UWB indoor positioning system 100 includes UWB beacons 102, also referred to as anchors, installed across an indoor space 120, for example but not limited to across a ceiling 122 in the indoor space 120. UWB refers to frequency bands greater than 500 MHz, and the UWB beacons 102 are configured to perform wireless communication in any UWB bandwidth. The UWB indoor positioning system 100 further includes at least one UWB tag 104, also referred to as a ranger, configured to wirelessly communicate with the UWB beacons 102 such that a computing device 111 executing a control software 112, such as a compute module located/executed/hosted in the cloud 108 and in communication with the UWB beacons 102, may determine/track the location of the UWB tag 104 and/or enable or disable a building environment device and/or a building security device based on such communication. In some aspects, such processing and location determination may be alternatively and/or additionally performed at least partially in a distributed manner by the UWB beacons 102 and/or the UWB tags 104 and/or the control software 112 executed by a computer device local to the indoor space 120.

In an aspect, each UWB tag 104 may be assigned to an asset or entity in, or movable into, the indoor space 120. In an aspect, for example, each UWB tag 104 may be assigned to and carried by an occupant 106 of the indoor space 120. In this aspect, the determined location/position of the UWB tag 104 may be indicative of a location/position of the occupant 106 within the indoor space 120. The computing device 111 executing the control software 112 in communication with one or more of the UWB beacons 102, and/or the UWB beacons 102 themselves, may use characteristics of UWB radiofrequency (RF) signals (e.g., TOA and/or TDOA) to find a three-dimensional (3D) position of the UWB tag 104 in the indoor space 120. Further, the computing device 111 and/or the one or more UWB beacons 102 may then update the corresponding location information in the control software 112. In an aspect, a mobile application (app) 114 running on a mobile device 110 of the occupant 106 may receive the location information from the control software 112, for example, through a WiFi or cellular communication, so that the mobile app 114 is synchronized (synch' ed) with a tag identifier (ID) associated with the UWB tag 104 and thereby with the occupant 106. The mobile app 114 may allow the occupant 106 to control and/or request and/or automatically be granted or not granted functionality associated with one or more building environment devices and/or one or more building security devices, e.g., based on the position, tag ID, and corresponding permissions associated with the UWB tag 104.

UWB Beacon/Tag Transmission Rate Control

In an aspect, the UWB beacons 102 in the indoor space 120 may be programmed/configured to ping all UWB tags 104 at all times. In an aspect, the UWB beacons 102 may be programmed/configured to ping the UWB tags 104 at a frequency that provides a location accuracy that complies with or is related to a fire rating associated with the indoor space 120. Alternatively and/or additionally, each UWB beacon 102 may be programmed/configured to vary the frequency of pinging the UWB tags 104 based on the last relative location of the UWB tags 104 with respect to that UWB beacon 102. For example, the UWB beacons 102 may be programmed/configured to reduce the frequency of pinging the UWB tags 104 that have been last detected to be relatively far from the UWB beacons 102, and increase the frequency of pinging the UWB tags 104 that have been detected to get relatively closer to the UWB beacons 102. By reducing unnecessary pinging of the UWB tags 104, the present aspects allow for extending the operating life of a battery 105 powering a UWB tag 104.

Accordingly, in an aspect, for example, a UWB indoor positioning method may include exchanging ranging signals at a first rate between a UWB beacon and a UWB tag; determining a relative distance between the UWB tag and the UWB beacon based on the ranging signals; selecting, based on the relative distance between the UWB tag and the UWB beacon, a second rate for exchanging subsequent ranging signals between the UWB beacon and the UWB tag, where the second rate is inversely proportional to the relative distance; and exchanging the subsequent ranging signals at the second rate between the UWB beacon and the UWB tag.

In an aspect, the UWB tag 104 may be configured to determine proximity to a point of interest, for example, using heading/direction and/or velocity data. The point of interest may be, for example, an entrance door 116 through which the occupant 106 is intending to pass, where the occupant 106 needs to unlock the entrance door 116 via the UWB tag 104. In an aspect, in response to determining a relative proximity of the UWB tag 104 to the entrance door 116, the UWB tag 104 may increase the UWB transmission rate of the UWB tag 104 to achieve further position accuracy for access control to the entrance door 116. Accordingly, the present aspects limit the use of UWB high transmission rate to situations that require high positioning accuracy. By intelligently varying the UWB transmission rate of the UWB tag 104, the power consumption of the UWB tag 104 may be reduced, thereby allowing for extended battery life of the UWB tag 104.

In a further aspect, in response to determining that the UWB tag 104 is moving toward a point of interest, the UWB tag 104 may increase its UWB transmission rate, and in response to determining that the UWB tag 104 is moving away from a point of interest, the UWB tag 104 may decrease its UWB transmission rate.

Optionally, the change in the transmission rate may be smooth and continuous or may be step-wise.

In an aspect, the decision to change the UWB transmission rate of the UWB tag 104 and/or change the UWB transmission rate of the UWB beacons 102 may be made by the control software 112 which may be running in the cloud 108, and the decision may be handed down to the UWB beacons 102 and/or the UWB tag 104 to adjust their corresponding rates.

In an aspect, for example, when the occupant 106 is in the proximity of an entrance door in the UWB indoor positioning system 100, the UWB transmission rate of the UWB beacons 102 and the UWB tag 104 may be configured to determine the location of the occupant 106 at such a high precision that indicates which side of the entrance door the occupant 106 is located. Accordingly, for example, in an active shooter lock-down situation or in a prison environment, the UWB indoor positioning system 100 may appropriately determine whether or not to open the entrance door 116 for the occupant 106 depending on which side of the entrance door 116 the occupant 106 is located.

In an aspect, the decision to allow the occupant 106 through the entrance door 116 may further be based on factors other than location, for example, may be further based on the time of day. In this aspect, a learning algorithm may be used to identify habits of the occupant 106 based on the time of day.

Accordingly, in an aspect, a UWB indoor positioning method may include exchanging ranging signals at a first rate between a UWB beacon and a UWB tag; determining a relative heading, velocity, or distance of the UWB tag with respect to a point of interest based on the ranging signals; selecting, based on the relative heading, velocity, or distance of the UWB tag with respect to the point of interest, a second rate for subsequent ranging signals between the UWB beacon and the UWB tag, wherein the second rate is higher than the first rate in response to the relative heading, velocity, or distance indicating that the UWB tag has moved or is moving toward the point of interest, wherein the second rate is lower than the first rate in response to the relative heading, velocity, or distance indicating that the UWB tag has moved or is moving away from the point of interest; and exchanging the subsequent ranging signals at the second rate between the UWB beacon and the UWB tag.

In an alternative and/or additional aspect, a movement detector such as an accelerometer in the UWB tag 104 or in the mobile device 110 may be used to control the UWB transmission rate of the UWB tag 104. For example, based on the readings of an accelerometer in the UWB tag 104 or in the mobile device 110, the UWB transmission rate of the UWB tag 104 may be increased when the UWB tag 104 and/or the occupant 106 who is associated with the UWB tag 104 are identified as moving as compared to when the UWB tag 104 and/or the occupant 106 who is associated with the UWB tag 104 are identified as being stationary.

Accordingly, in an aspect, a UWB indoor positioning method may include exchanging ranging signals at a first rate between a UWB beacon and a UWB tag; determining movement information of the UWB tag based on a movement detection device within or associated with the UWB tag; selecting, based on the movement information, a second rate for subsequent ranging signals between the UWB beacon and the UWB tag, wherein the second rate is higher than the first rate in response to the movement information indicating that the UWB tag is moving or speeding up, wherein the second rate is lower than the first rate in response to the movement information indicating that the UWB tag has stopped or is slowing down; and exchanging the subsequent ranging signals at the second rate between the UWB beacon and the UWB tag.

UWB Positioning to Improve Another Type of Positioning

In an aspect, the UWB indoor positioning system 100 may be used in conjunction with another less accurate positioning system to improve the accuracy of the less accurate positioning system such as a phone-based location technology, e.g., a magnetometer, or other indoor positioning technologies such as WiFi location technologies, Bluetooth or BLE location technologies, etc. For example, the UWB tag 104 may be configured to transmit UWB signals periodically, occasionally/infrequently, or on-demand/as-triggered, to allow for accurate UWB positioning information to be used to re-calibrate the less accurate positioning system. For example, a magnetometer reading in a phone-based positioning system may get distorted by a metal in the vicinity. However, if occasionally re-calibrated based on the readings of the UWB tag 104, the magnetometer in the mobile device 110 may be able to provide a fairly accurate location of the occupant 106. Accordingly, high positioning accuracy may be achieved even with infrequent use of the UWB tag 104, e.g., every 5 minutes, thus allowing for extended battery life of the UWB tag 104.

Accordingly, in an aspect, a positioning method may include exchanging, by a beacon, UWB ranging signals with a tag having a UWB communication component; determining a relative location of the tag based on the UWB ranging signals received by the beacon from the tag; calibrating a non-UWB positioning system based on the relative location; and tracking the tag by the non-UWB positioning system.

Alternatively and/or additionally, the less accurate positioning system may be used for positioning when a very accurate location determination is not required and a crude position determination is sufficient, and the UWB positioning may be used only when/where more accurate positioning functionality is desired/required, such as when the occupant 106 is at or near or approaching a point of interest such as the entrance door 116. In an aspect, the less accurate positioning system may update the estimated location of the occupant 106 at the control software 112 in the cloud 108 at a first frequency, while the UWB tag 104 may update a more accurate estimated location of the occupant 106 at the control software 112 in the cloud 108 at a second frequency lower than the first frequency. Accordingly, the present aspects limit the use of UWB tag 104 to situations that require high positioning accuracy. By intelligently limiting the use of the UWB tag 104 to such situations, the power consumption of the UWB tag 104 may be reduced, thereby allowing for extended battery life of the UWB tag 104.

Accordingly, in an aspect, a positioning method may include detecting a position of a UWB tag by a non-UWB positioning system; determining a relative location of the UWB tag with reference to a point of interest based on the detected position; exchanging ranging signals with the UWB tag, by a UWB beacon, in response to the relative location being within a proximity threshold of the point of interest; and tracking the relative location of the UWB tag with reference to the point of interest based on the ranging signals received by the UWB beacon from the UWB tag.

In an aspect, for example, phone-based positioning functionality may be implemented using the mobile app 114 and a magnetometer in the mobile device 110. When the mobile app 114 is running in the background, the frequency at which the mobile app 114 pulls location information from the magnetometer in the mobile device 110 may be limited by a manufacturer of the mobile device 110 in order to conserve battery and/or processing resources of the mobile device 110. In this case, the location update frequency of the UWB tag 104 may be increased to make up for such update frequency limitation of the positioning functionality provided by the mobile device 110. Alternatively, when the mobile app 114 is being actively used on the mobile device 110 and/or running in the foreground, there may be lower or no manufacturer-imposed limitation on the use of system resources by the mobile app 114. In this case, the location update frequency of the UWB tag 104 may be decreased in response to less update frequency limitation on the positioning functionality provided by the mobile device 110.

Accordingly, in an aspect, a positioning method may include detecting a location of a UWB tag by a mobile application in a mobile device associated with the UWB tag; adjusting a location update rate of the UWB tag based on a status of the mobile application, wherein the adjusting increases the location update rate in response to the mobile application running in the background and decreases the location update rate in response to the mobile application running in the foreground; and tracking the location of the UWB tag at the location update rate based on signals exchanged between a UWB beacon and the UWB tag.

In an aspect, the UWB beacons 102 and the UWB tag 104 may both implement a second less accurate positioning technology. For example, the UWB beacons 102 and the UWB tag 104 may both implement combined BLE/UWB functionality. In this aspect, instead of performing UWB communication at all times, the UWB communication scheme may only be activated on the UWB tag 104 when the UWB tag 104 is close to a point of interest, and the BLE communication scheme may be activated on the UWB tag 104 when the UWB tag 104 is away from the point of interest. In an aspect, the UWB tag 104 may further be configured to transmit periodically to correct the BLE drift in the BLE positioning functionality of the UWB tag 104. In an aspect where the UWB indoor positioning system 100 includes or works in cooperation with another positioning system such as BLE, BLE positioning may first be used to determine a crude or high level position of the UWB tag 104, and then UWB positioning may be used to fine tune the determined position to a higher accuracy. Accordingly, high positioning accuracy may be achieved even with intermittent use of the UWB tag 104, thus allowing for extended battery life of the UWB tag 104.

Authentication Functionality Supplemented by UWB Positioning

In an aspect, the UWB beacons 102 may operate in combination with other security equipment such as the security camera 118 to implement a multi-factor authentication scheme. For example, the security camera 118 may detect a face of the occupant 106 and communicate such information to the control software 112 on premise or in the cloud 108. In response, the control software 112 may direct a UWB beacon 102 in an area associated with the recognized face, e.g., at or near the entrance door 116 where the security camera 118 is installed, to ping or wake up the UWB tags 104 in such area and request the UWB tags 104 to transmit location information. Accordingly, the tag ID of the UWB tag 104 may be correlated with an ID associated with the recognized face, thereby implementing a two-factor authentication scheme. Then, the entrance door 116 may be opened only in response to a match between a recognized face detected by the security camera 118 at the entrance door 116 and the tag ID associated with the UWB tag 104 transmitting at the entrance door 116. In FIG. 1, the tag ID of the UWB tag 104 identifies the occupant 106. Therefore, the entrance door 116 may be opened only in response to a match between a recognized face detected by the security camera 118 at the entrance door 116 and the occupant 106. Such multi-factor authentication may prevent misuse of the UWB tag 104 by an illegitimate entity to gain privileges through the UWB tag 104.

Accordingly, in an aspect, an authentication method may include determining a location of a UWB tag based on signals received by a UWB beacon from the UWB tag; determining an identifier (ID) associated with the UWB tag; determining biometric data of an entity substantially located at the location of the UWB tag; and authenticating the entity in response to the biometric data being associated with the ID associated with the UWB tag.

Alternatively and/or additionally, any other biometric detection mechanism may be used to implement such multi-factor authentication. Alternatively and/or additionally, multi-factor authentication may be implemented by a combination of a low accuracy positioning system such as BLE and an accurate UWB positioning system. For example, in less security-sensitive areas in a building such as a yard, a BLE or phone-based positioning system may be used to corroborate a detection made by a security camera, while in more security-sensitive locations in the same building such as at the entrance door 116, the UWB positioning system as implemented by the UWB tag 104 may be used to corroborate a detection made by the security camera 118. Accordingly, the present aspects limit the use of UWB tag 104 to situations that require higher security. By intelligently limiting the use of the UWB tag 104 to such situations, the power consumption of the UWB tag 104 may be reduced, thereby allowing for extended battery life of the UWB tag 104.

Perimeter Security Functionality Supplemented by UWB Positioning

Figure 2:
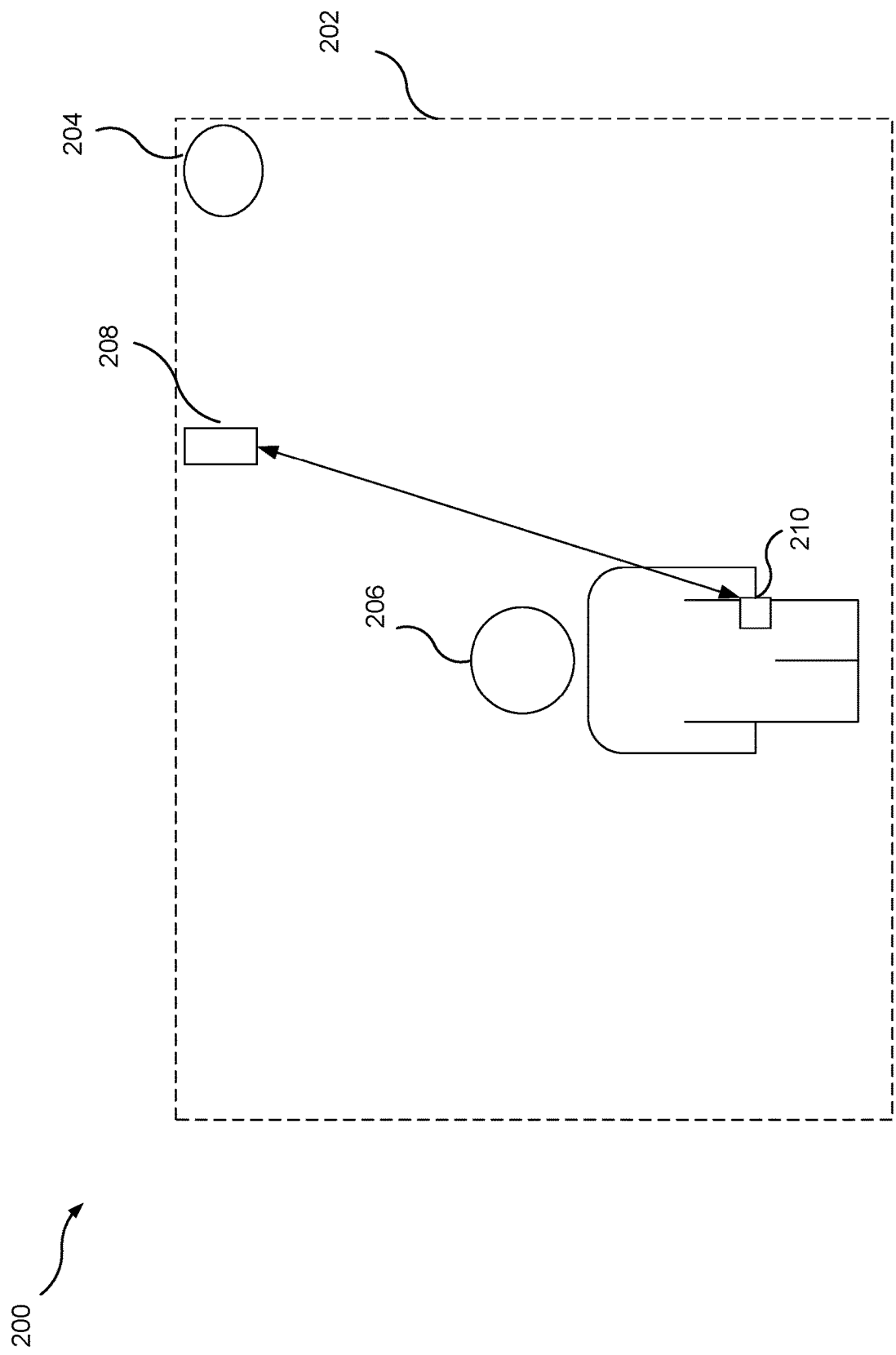
FIG. 2 is a schematic diagram of an example security system that also uses UWB positioning functionality.

In an aspect, security functionality provided in a monitored area may be enhanced by UWB positioning functionality providing related information in that monitored area. For example, referring to FIG. 2, in an aspect, a security system 200 may monitor an area 202 via at least one security device 204. For example, the security device 204 may be a security camera, a passive infra-red (PIR) detector, or any other device operable to detect security events related to a presence and/or a movement of an object 206 in the monitored area 202. Alternatively and/or additionally, the security device 204 may be an optical or other type of tripwire around a perimeter of the monitored area 202 or any other device operable to detect security events indicating that the object 206 has crossed a perimeter line of the monitored area 202. Upon detection of a security event by the security device 204, the security system 200 may request a UWB beacon 208 within or associated with the monitored area 202 to query UWB tags 210 in the monitored area 202. In response, the UWB beacon 208 may activate/wake up nearby UWB tags 210 to identify legitimate entities/activities in the monitored area 202. In an aspect, for example, in response to receiving an alarm input from a tripwire or a security camera, the UWB beacon 208 may request the UWB tags 210 in the monitored area 202 to transmit their respective locations. Such locations may then be used to validate that what has been detected by the alarm is an allowed event, e.g., a legitimate person associated with a responding UWB tag 210 has tripped the wire or crossed the field of view of the security camera.

Accordingly, in an aspect, a security method may include determining a security event in a monitored area; transmitting ranging signals, by one or more UWB beacons, to query a location of UWB tags in the monitored area; and determining whether a UWB tag located in the monitored area by the UWB beacons is associated with the security event.

Geo-Fencing Functionality in UWB Positioning

Figure 3:
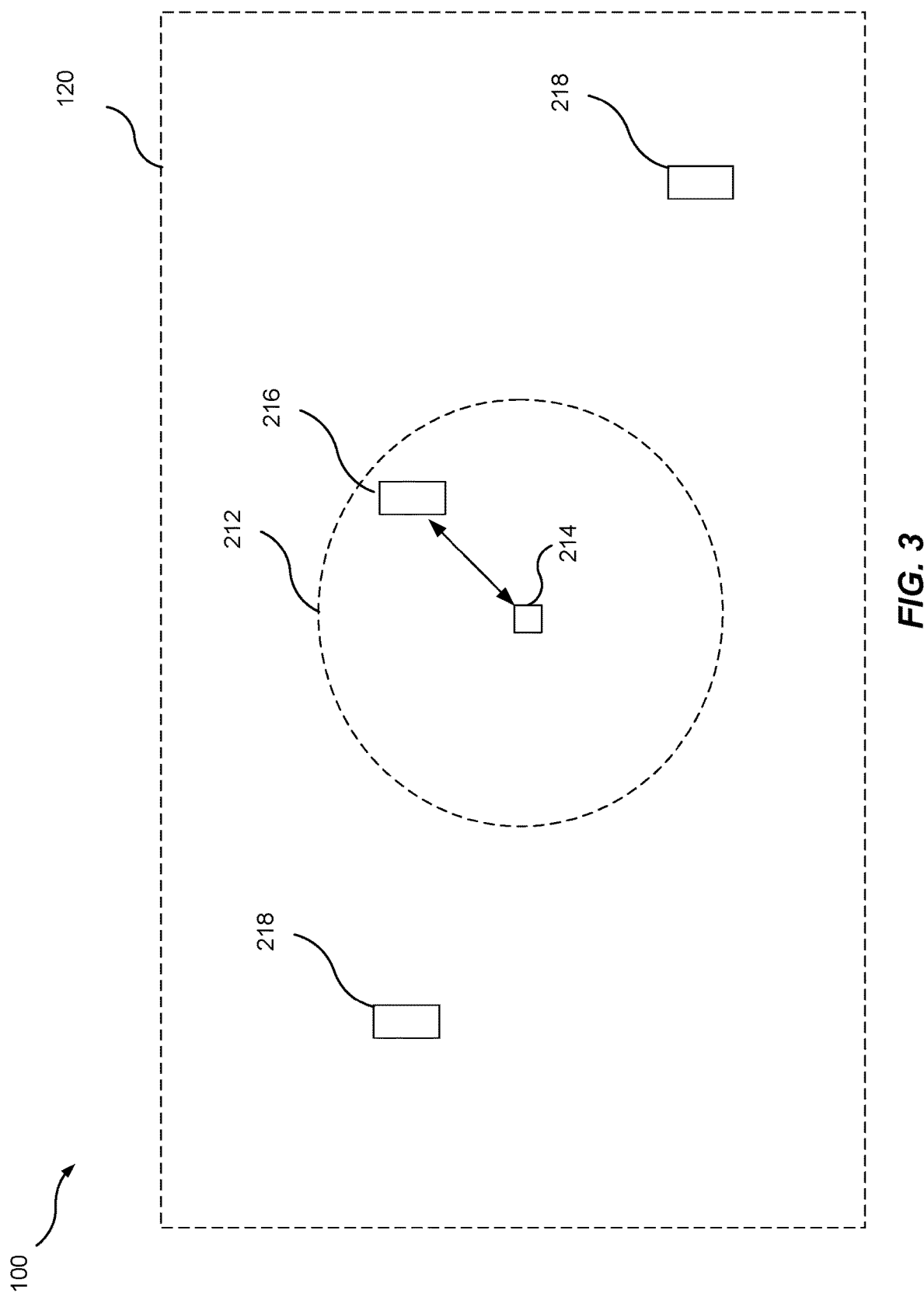
FIG. 3 is a schematic diagram of the example UWB positioning system of FIG. 1 further including geo-fencing functionality.

Referring to FIG. 3, in an aspect, the UWB indoor positioning system 100 may further implement geo-fencing functionality for more efficiently using UWB beacons/tags. A geo-fence refers to a virtual fence/perimeter defined for a corresponding geographic area. For example, in an aspect, a dynamic geo-fence 212, e.g., a few meters wide, may be defined based on a current location of a UWB tag 214 in the indoor space 120. The dynamic geo-fence 212 may then be used to control the ranging rate to the UWB tag 214. For example, only the UWB beacon 216 which is within a specified range, i.e., within the dynamic geo-fence 212, of the UWB tag 214 may be configured to transmit UWB signals to ask for the location of the UWB tag 214, and other UWB beacons 218 which are outside the dynamic geo-fence 212 may be prevented from pinging the UWB tag 214. This will reduce the communication/response burden on the UWB tag 214 and will therefore prolong the battery life the UWB tag 214. Such power preservation benefits are particularly significant since some UWB beacons 218 may have a range of about 50 or 100 meters and may therefore unnecessarily ping the UWB tag 214 if not excluded based on the dynamic geo-fence 212 around the UWB tag 214.

Accordingly, in an aspect, a UWB positioning method may include defining a geo-fence based on a position of a UWB tag; selecting a set of UWB beacons for exchanging ranging signals with the UWB tag, wherein the set includes one or more UWB beacons located within a proximity threshold of the geo-fence and excludes any UWB beacons located outside the proximity threshold of the geo-fence; exchanging ranging signals between the UWB tag and the set of UWB beacons; and tracking a location of the UWB tag based on the ranging signals.

Location Update Rate Control Based on Mobile App

Referring back to FIG. 1, in an aspect, the frequency of the location refresh update by the UWB tag 104 may be controlled based on feedback from the mobile app 114. For example, if the occupant 106 is not logged into the mobile app 114, less frequent location updates may be sufficient. Accordingly, the UWB tag 104 may not transmit signals or may transmit infrequently when the mobile app 114 is not being used by the occupant 106.

Accordingly, in an aspect, a positioning method may include detecting a status of execution of a mobile application in a mobile device associated with a UWB tag; adjusting a location update rate of the UWB tag based on the status of execution of the mobile application, wherein the adjusting includes increasing the location update rate in response to the status of the execution of the mobile application indicating an executing status, a running in the foreground status, or a user logged in status, and wherein the adjusting includes decreasing the location update rate in response to the status of execution of the mobile application indicating a not executing status, a running in the background status, or a user not logged in status; and tracking a location of the UWB tag at the location update rate based on signals exchanged between a UWB beacon and the UWB tag.

Alternatively and/or additionally, the frequency of the location refresh update by the UWB tag 104 may further be controlled based on an asset type associated with the UWB tag 104. For example, the update frequency may be higher for more mobile personnel and lower for more sedentary personnel. As another example, for example, in a hospital environment, the update frequency may be lower for large hardware assets such as medical imaging devices as compared to human assets such as doctors and nurses. As yet another example, the update frequency may be higher for more expensive assets as compared to less expensive assets.

In an aspect, the mobile device 110 may be configured to establish a peer-to-peer communication with the UWB beacons 102 and/or with the UWB tag 104 such that the mobile app 114 may send and/or receive location-related or other information over such a peer-to-peer communication.

UWB Tag and Beacon Packaging

In some aspects, the UWB tag 104 may be configured as a key fob, a card/card holder, a wearable, e.g., on a wrist or arm or hanging from the neck of the occupant 106, etc. Alternatively, the UWB tag 104 may be attachable to the mobile device 110 of the occupant 106, e.g., attachable to the back of a smartphone. In this case, optionally, the UWB tag 104 may be configured to harvest energy from the mobile device 110 of the occupant 106.

In an aspect, the UWB beacons 102 communicate via RF, and therefore do not need hardwired network connections and may be installed/mounted within an enclosure of an existing fixtures or a positioning or security device such as an enclosure of an exit sign, a PIR detector, a thermostat, a WiFi beacon, a closed circuit television (CCTV) security camera 118, etc. Accordingly, installation time may be reduced, maintenance may be eased, and insulation may be improved.

Figure 4:
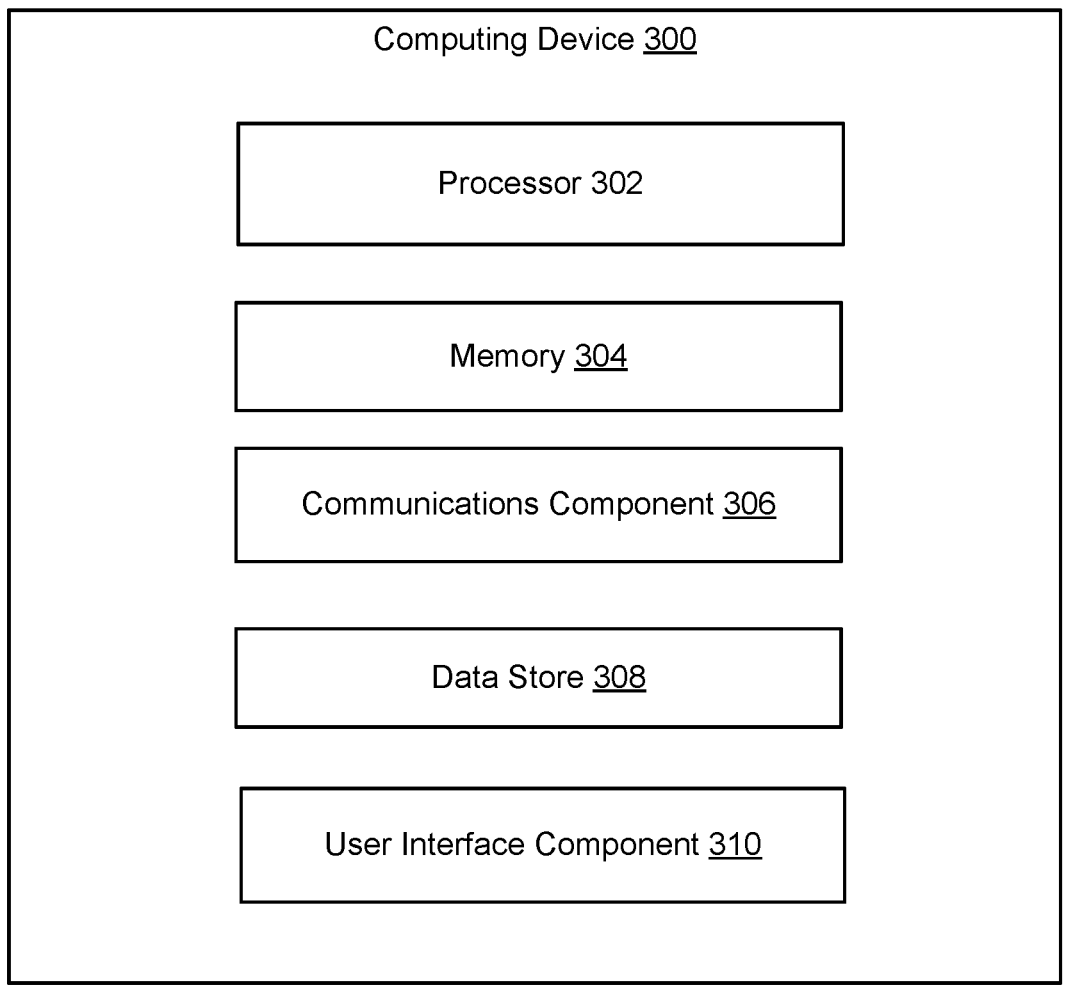
FIG. 4 is a block diagram of an example computing device which may implement a component in the example UWB positioning system of FIG. 1.

FIG. 4 illustrates an example block diagram providing details of computing components in a computing device 300 that may implement all or a portion of the UWB beacons 102, 208, 216, 218, the UWB tags 104, 210, 214, one or more components in the cloud 108, the mobile device 110, the security camera 118, the security device 204, the computing device 111, or any other component in the UWB indoor positioning system 100 or in the security system 200. The computing device 300 includes a processor 302 which may be configured to execute or implement software, hardware, and/or firmware modules that perform any indoor positioning, security, or other functionality described herein with reference to the UWB beacons 102, 208, 216, 218, the UWB tags 104, 210, 214, the cloud 108, the mobile device 110, the security camera 118, the security device 204, the computing device 111, or any other component in the UWB indoor positioning system 100 or in the security system 200.

The processor 302 may be a micro-controller and/or may include a single or multiple set of processors or multi-core processors. Moreover, the processor 302 may be implemented as an integrated processing system and/or a distributed processing system. The computing device 300 may further include a memory 304, such as for storing local versions of applications being executed by the processor 302, related instructions, parameters, etc. The memory 304 may include a type of memory usable by a computer, such as random access memory (RAM), read only memory (ROM), tapes, magnetic discs, optical discs, volatile memory, non-volatile memory, and any combination thereof. Additionally, the processor 302 and the memory 304 may include and execute an operating system executing on the processor 302, one or more applications, display drivers, etc., and/or other components of the computing device 300.

Further, the computing device 300 may include a communications component 306 that provides for establishing and maintaining communications, such as UWB communications, with one or more other devices, parties, entities, etc. utilizing hardware, software, and services. The communications component 306 may carry communications between components on the computing device 300, as well as between the computing device 300 and external devices, such as devices located across a communications network and/or devices serially or locally connected to the computing device 300. For example, the communications component 306 may include one or more buses, and may further include transmit chain components and receive chain components associated with a wireless or wired transmitter and receiver, respectively, operable for interfacing with external devices.

Additionally, the computing device 300 may include a data store 308, which can be any suitable combination of hardware and/or software, that provides for mass storage of information, databases, and programs. For example, the data store 308 may be or may include a data repository for applications and/or related parameters not currently being executed by processor 302. In addition, the data store 308 may be a data repository for an operating system, application, display driver, etc., executing on the processor 302, and/or one or more other components of the computing device 300.

The computing device 300 may also include a user interface component 310 operable to receive inputs from a user of the computing device 300 and further operable to generate outputs for presentation to the user (e.g., via a display interface to a display device). The user interface component 310 may include one or more input devices, including but not limited to a keyboard, a number pad, a mouse, a touch-sensitive display, a navigation key, a function key, a microphone, a voice recognition component, or any other mechanism capable of receiving an input from a user, or any combination thereof. Further, the user interface component 310 may include one or more output devices, including but not limited to a display interface, a speaker, a haptic feedback mechanism, a printer, any other mechanism capable of presenting an output to a user, or any combination thereof.

Figure 5:
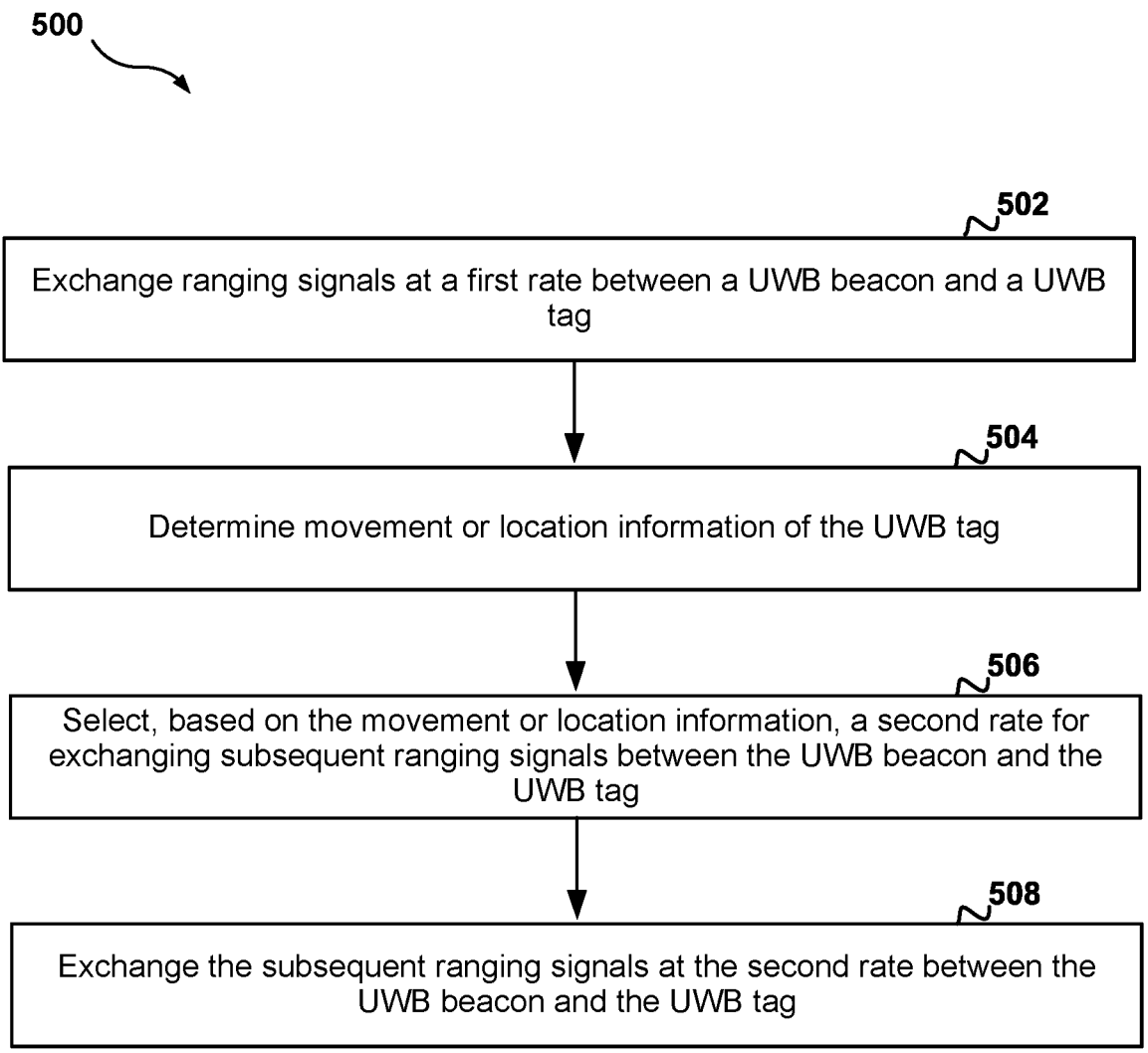
FIG. 5 is a flow diagram of an example method of UWB positioning.

FIG. 5 is a flowchart of a method 500 of operation of the computing device 300. The method 500 may implement the functionality described herein with reference to FIGS. 1-4 above, and may be performed by one or more components of the computing device 300 or the UWB beacons 102, 208, 216, 218, the UWB tags 104, 210, 214, one or more components in the cloud 108, the mobile device 110, the security camera 118, the security device 204, the computing device 111, or any other component in the UWB indoor positioning system 100 or in the security system 200 as described herein with reference to FIGS. 1-4 above.

At 502, the method 500 of UWB positioning includes exchanging ranging signals at a first rate between a UWB beacon and a UWB tag. For example, in an aspect, the communications component 306 of the computing device 300 (which may implement a UWB beacon 102, 208, 216, 218) may exchange ranging signals at a first rate with a UWB tag 104, 210, 214.

At 504, the method 500 further includes determining movement or location information of the UWB tag. For example, in an aspect, the processor 302 of the computing device 300 (which may implement a UWB beacon 102, 208, 216, 218 or a computing device 111 executing a control software 112, such as a compute module located/executed/hosted in the cloud 108) may determine movement or location information of the UWB tag 104, 210, 214. For example, in an aspect, the communications component 306 may communicate ranging signals with the UWB tag 104, and the processor 302 may determine the location of the UWB tag 104 using characteristics of UWB RF signals (e.g., TOA and/or TDOA) to find a 3D position of the UWB tag 104 in the indoor space 120. In another aspect, for example, the communications component 306 may communicate successive ranging signals with the UWB tag 104, and the processor 302 may determine movement of the UWB tag 104 based on a change in the 3D position of the UWB tag 104 in the indoor space 120.

At 506, the method 500 further includes selecting, based on the movement or location information, a second rate for exchanging subsequent ranging signals between the UWB beacon and the UWB tag. For example, in an aspect, the processor 302 of the computing device 300 may select, based on the movement or location information, a second rate for exchanging subsequent ranging signals with the UWB tag 104, 210, 214. For example, in another non-limiting aspect, the processor 302 may lower the rate when the UWB tag 104, 210, 214 is moving away from the computing device 300 (which may implement a UWB beacon 102, 208, 216, 218), or may raise the rate when the UWB tag 104, 210, 214 is moving toward the computing device 300 (which may implement a UWB beacon 102, 208, 216, 218).

At 508, the method 500 further includes exchanging the subsequent ranging signals at the second rate between the UWB beacon and the UWB tag. For example, in an aspect, the communications component 306 of the computing device 300 may exchange the subsequent ranging signals at the second rate with the UWB tag 104, 210, 214.

Optionally, the determining at 504 may include determining a relative distance between the UWB tag and the UWB beacon based on the ranging signals.

Optionally, the selecting at 506 may include selecting, based on the relative distance between the UWB tag and the UWB beacon, the second rate for exchanging subsequent ranging signals between the UWB beacon and the UWB tag. The second rate may be inversely proportional to the relative distance.

Optionally, the determining at 504 may include determining a relative heading, velocity, or distance of the UWB tag with respect to a point of interest based on the ranging signals. For example, in an aspect, the processor 302 may be configured to determine proximity to a point of interest, for example, using heading/direction and/or velocity data related to the UWB tag 104. The point of interest may be, for example, an entrance door 116 through which the occupant 106 is intending to pass, where the occupant 106 needs to unlock the entrance door 116 via the UWB tag 104.

Optionally, the selecting at 506 may include selecting, based on the relative heading, velocity, or distance of the UWB tag with respect to the point of interest, the second rate for subsequent ranging signals between the UWB beacon and the UWB tag. The second rate may be higher than the first rate in response to the relative heading, velocity, or distance indicating that the UWB tag has moved or is moving toward the point of interest. The second rate may be lower than the first rate in response to the relative heading, velocity, or distance indicating that the UWB tag has moved or is moving away from the point of interest. For example, in an aspect, in response to determining a relative proximity of the UWB tag 104 to the entrance door 116, the processor 302 may increase the UWB transmission rate of the UWB tag 104 to achieve further position accuracy for access control to the entrance door 116. Accordingly, the present aspects limit the use of UWB high transmission rate to situations that require high positioning accuracy. By intelligently varying the UWB transmission rate of the UWB tag 104, the power consumption of the UWB tag 104 may be reduced, thereby allowing for extended battery life of the UWB tag 104. In a further aspect, for example, in response to determining that the UWB tag 104 is moving toward a point of interest, the processor 302 may increase the UWB transmission rate, and in response to determining that the UWB tag 104 is moving away from a point of interest, the processor 302 may decrease the UWB transmission rate. Optionally, in an aspect, for example, the change in the transmission rate may be smooth and continuous or may be step-wise. In an aspect, for example, the decision to change the UWB transmission rate of the UWB tag 104 and/or change the UWB transmission rate of the UWB beacons 102 may be made by the control software 112 which may be running in the cloud 108, and the decision may be handed down to the UWB beacons 102 and/or the UWB tag 104 to adjust their corresponding rates.

Optionally, the determining at 504 may include determining movement information of the UWB tag based on a movement detection device within or associated with the UWB tag. For example, in an aspect, a movement detector such as an accelerometer in the UWB tag 104 or in the mobile device 110 may be used to control the UWB transmission rate of the UWB tag 104.

Optionally, the selecting at 506 may include selecting, based on the movement information, the second rate for subsequent ranging signals between the UWB beacon and the UWB tag. The second rate may be higher than the first rate in response to the movement information indicating that the UWB tag is moving or speeding up. The second rate may be lower than the first rate in response to the movement information indicating that the UWB tag has stopped or is slowing down. For example, in an aspect, based on the readings of an accelerometer in the UWB tag 104 or in the mobile device 110, the UWB transmission rate of the UWB tag 104 may be increased when the UWB tag 104 and/or the occupant 106 who is associated with the UWB tag 104 are identified as moving as compared to when the UWB tag 104 and/or the occupant 106 who is associated with the UWB tag 104 are identified as being stationary.

Optionally, the method 500 may further include detecting a location of the UWB tag by a mobile application in a mobile device associated with the UWB tag. In an aspect, for example, each UWB tag 104 may be assigned to and carried by an occupant 106 of the indoor space 120. In this aspect, a mobile app 114 running on a mobile device 110 of the occupant 106 may receive the location information from the control software 112, for example, through a WiFi or cellular communication, so that the mobile app 114 is synchronized with a tag ID associated with the UWB tag 104 and thereby with the occupant 106.

Optionally, the method 500 may further include adjusting a location update rate of the UWB tag based on a status of the mobile application. The adjusting may increase the location update rate in response to the mobile application running in the background and may decrease the location update rate in response to the mobile application running in the foreground. In an aspect, for example, when the mobile app 114 is running in the background, the frequency at which the mobile app 114 pulls location information from the magnetometer in the mobile device 110 may be limited by a manufacturer of the mobile device 110 in order to conserve battery and/or processing resources of the mobile device 110. In this case, the location update frequency of the UWB tag 104 may be increased to make up for such update frequency limitation of the positioning functionality provided by the mobile device 110. Alternatively, when the mobile app 114 is being actively used on the mobile device 110 and/or running in the foreground, there may be lower or no manufacturer-imposed limitation on the use of system resources by the mobile app 114. In this case, the location update frequency of the UWB tag 104 may be decreased in response to less update frequency limitation on the positioning functionality provided by the mobile device 110.

Optionally, the method 500 may further include tracking the location of the UWB tag at the location update rate based on signals exchanged between a UWB beacon and the UWB tag. For example, in an aspect, the location of the UWB tag 104 may be tracked at the new location update rate.

Optionally, the method 500 may further include detecting a status of execution of a mobile application in a mobile device associated with the UWB tag. For example, in an aspect, if the occupant 106 is not logged into the mobile app 114, less frequent location updates may be sufficient. Accordingly, the UWB tag 104 may not transmit signals or may transmit infrequently when the mobile app 114 is not being used by the occupant 106. Accordingly, the processor 302 may detect a status of execution of the mobile app 114 in the mobile device 110 associated with the UWB tag 104.

Optionally, the method 500 may further include adjusting a location update rate of the UWB tag based on the status of execution of the mobile application. The adjusting may include increasing the location update rate in response to the status of the execution of the mobile application indicating an executing status, a running in the foreground status, or a user logged in status. The adjusting may include decreasing the location update rate in response to the status of execution of the mobile application indicating a not executing status, a running in the background status, or a user not logged in status. For example, in one non-limiting aspect, if the occupant 106 is not logged into the mobile app 114, less frequent location updates may be sufficient. Accordingly, the UWB tag 104 may not transmit signals or may transmit infrequently when the mobile app 114 is not being used by the occupant 106.

Optionally, the method 500 may further include tracking a location of the UWB tag at the location update rate based on signals exchanged between a UWB beacon and the UWB tag. For example, in an aspect, the location of the UWB tag 104 may be tracked at the new location update rate.

Optionally, the method 500 may further include defining a geo-fence based on a position of the UWB tag. For example, in an aspect, a dynamic geo-fence 212, e.g., a few meters wide, may be defined based on a current location of a UWB tag 214 in the indoor space 120.

Optionally, the method 500 may further include selecting a set of UWB beacons for exchanging ranging signals with the UWB tag. The set may include one or more UWB beacons located within a proximity threshold of the geo-fence and may exclude any UWB beacons located outside the proximity threshold of the geo-fence. For example, in an aspect, only the UWB beacon 216 which is within a specified range, i.e., within the dynamic geo-fence 212, of the UWB tag 214 may be configured to transmit UWB signals to ask for the location of the UWB tag 214, and other UWB beacons 218 which are outside the dynamic geo-fence 212 may be prevented from pinging the UWB tag 214.

Optionally, the method 500 may further include exchanging ranging signals between the UWB tag and the set of UWB beacons. In an aspect, for example, the UWB tag 104 may exchange ranging signals only with the UWB beacon 216 which is within a specified range, i.e., within the dynamic geo-fence 212, of the UWB tag 214.

Optionally, the method 500 may further include tracking a location of the UWB tag based on the ranging signals. For example, in an aspect, the location of the UWB tag 104 is tracked based on the ranging signals exchanged with the UWB beacon 216 which is within a specified range, i.e., within the dynamic geo-fence 212, of the UWB tag 214.

Optionally, the method 500 may further include controlling a building environment device or a building security device based on a position of the UWB tag. For example, in an aspect, the position of the UWB tag 104, 210, 214, which is used to track the position of an object, such as a person moving indoors, may be used to efficiently condition the environment in a building based on the location of occupants, e.g., to adjust lighting, air conditioning, and/or to perform presence/security monitoring (e.g., responsive to an alarm or detection of an object in the building, the UWB beacon performing ranging signalling to identify and locate UWB tags in the area of the alarm/detection), and/or to provide privileges to the occupants of a building based on an identified UWB tag being correlated to another authentication factor (e.g., identification by a camera or sensor or other security equipment), e.g., to open an entrance door, unlock a resource such as a computer, printer, or other machine, etc.

Optionally, exchanging the ranging signals at 502 may include exchanging the ranging signals at the first rate between the UWB beacon and the UWB tag and between one or more additional UWB beacons and the UWB tag.

Optionally, selecting the second rate at 506 may include selecting the second rate for exchanging the subsequent ranging signals between the UWB beacon and the UWB tag and between the one or more additional UWB beacons and the UWB tag.

Optionally, exchanging the subsequent ranging signals at 508 may include exchanging the subsequent ranging signals at the second rate between the UWB beacon and the UWB tag and between the one or more additional UWB beacons and the UWB tag.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." The word "exemplary" is used herein to mean "serving as an example, instance, or illustration." Any aspect described herein as "exemplary" is not necessarily to be construed as preferred or advantageous over other aspects. Unless specifically stated otherwise, the term "some" refers to one or more. Combinations such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C.

Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. The words "module," "mechanism," "element," "device," and the like may not be a substitute for the word "means." As such, no claim element is to be construed as a means plus function unless the element is expressly recited using the phrase "means for."

What is claimed is:

1. An ultra-wideband "UWB" positioning method, comprising:
   exchanging ranging signals at a first rate between a UWB beacon and a UWB tag associated with a person;
   determining movement information of the UWB tag based on a movement detection device within a mobile device of the person that is associated with the UWB tag, wherein the mobile device is different than the UWB tag;
   selecting, based on the movement information, a second rate for exchanging subsequent ranging signals between the UWB beacon and the UWB tag; and
   exchanging the subsequent ranging signals at the second rate between the UWB beacon and the UWB tag.

2. The UWB positioning method of claim 1, wherein the second rate is higher than the first rate in response to the movement information indicating that the UWB tag is moving.

3. The UWB positioning method of claim 1, wherein the second rate is higher than the first rate in response to the movement information indicating that the UWB tag is speeding up.

4. The UWB positioning method of claim 1, wherein the second rate is lower than the first rate in response to the movement information indicating that the UWB tag has stopped.

5. The UWB positioning method of claim 1, wherein the second rate is lower than the first rate in response to the movement information indicating that the UWB tag is slowing down.

6. The UWB positioning method of claim 1, wherein the second rate is lower than the first rate in response to the movement information indicating that the UWB tag is moving away from a point of interest in a building, wherein the second rate is higher than the first rate in response to the movement information indicating that the UWB tag is moving toward the point of interest in the building.

7. The UWB positioning method of claim 6, wherein the point of interest comprises the UWB beacon or a virtual geographic boundary.

8. The UWB positioning method of claim 6, wherein the point of interest comprises a geo-fence.

9. The UWB positioning method of claim 1, wherein the second rate is lower than the first rate in response to the movement information indicating that the UWB tag is moving from a first location toward a second location that has a lower priority for accurate positioning as compared to the first location, wherein the second rate is higher than the first rate in response to the movement information indicating that the UWB tag is moving from the second location toward the first location.

10. The UWB positioning method of claim 9, wherein the first location and/or the second location are defined by a virtual geographic boundary or a geo-fence.

11. An ultra-wideband "UWB" beacon apparatus comprising:
   a UWB communication component configured for exchanging ranging signals at a first rate with a UWB tag apparatus associated with a person;
   a controller configured for:
      determining movement information of the UWB tag apparatus based on a movement detection device within a mobile device of the person that is associated with the UWB tag apparatus, wherein the mobile device is different than the UWB tag apparatus; and
      selecting, based on the movement information, a second rate for exchanging subsequent ranging signals between the UWB beacon apparatus and the UWB tag apparatus; and
   the UWB communication component further configured for exchanging the subsequent ranging signals at the second rate between the UWB beacon apparatus and the UWB tag apparatus.

12. The UWB beacon apparatus of claim 11, wherein the second rate is higher than the first rate in response to the movement information indicating that the UWB tag apparatus is moving.

13. The UWB beacon apparatus of claim 11, wherein the second rate is higher than the first rate in response to the movement information indicating that the UWB tag apparatus is speeding up.

14. The UWB beacon apparatus of claim 11, wherein the second rate is lower than the first rate in response to the movement information indicating that the UWB tag apparatus has stopped.

15. The UWB beacon apparatus of claim 11, wherein the second rate is lower than the first rate in response to the movement information indicating that the UWB tag apparatus is slowing down.

16. An ultra-wideband "UWB" tag apparatus associated with a person, comprising a communication component configured for:
   exchanging ranging signals at a first rate with a UWB beacon apparatus, causing the UWB beacon apparatus to determine movement information of the UWB tag apparatus based on a movement detection device within a mobile device of the person that is associated with the UWB tag apparatus, wherein the mobile device is different than the UWB tag apparatus, and select, based on the movement information, a second rate for exchanging subsequent ranging signals between the UWB beacon apparatus and the UWB tag apparatus; and
   exchanging the subsequent ranging signals at the second rate with the UWB beacon apparatus.

17. The UWB tag apparatus of claim 16, wherein the second rate is higher than the first rate in response to the movement information indicating that the UWB tag apparatus is moving.

18. The UWB tag apparatus of claim 16, wherein the second rate is higher than the first rate in response to the movement information indicating that the UWB tag apparatus is speeding up.

19. The UWB tag apparatus of claim 16, wherein the second rate is lower than the first rate in response to the movement information indicating that the UWB tag apparatus has stopped.

20. The UWB tag apparatus of claim 16, wherein the second rate is lower than the first rate in response to the movement information indicating that the UWB tag apparatus is slowing down.

* * * * *